(12) United States Patent
De Bellis

(10) Patent No.: US 9,174,056 B2
(45) Date of Patent: Nov. 3, 2015

(54) HEART STIMULATION DEVICE AND RESPECTIVE CONTROL SYSTEM

(75) Inventor: Ferruccio De Bellis, Rome (IT)

(73) Assignee: P.A. & M. PARTECIPAZIONI AZIONARIE & MANAGEMENT S.R.L., Rome (IT)

( * ) Notice: Subject to any disclaimer, the term of this patent is extended or adjusted under 35 U.S.C. 154(b) by 0 days.

(21) Appl. No.: 14/237,627

(22) PCT Filed: Jul. 24, 2012

(86) PCT No.: PCT/IB2012/053762
§ 371 (c)(1),
(2), (4) Date: Feb. 7, 2014

(87) PCT Pub. No.: WO2013/021301
PCT Pub. Date: Feb. 14, 2013

(65) Prior Publication Data
US 2014/0194940 A1    Jul. 10, 2014

(30) Foreign Application Priority Data
Aug. 8, 2011   (IT) .............................. RM2011A0429

(51) Int. Cl.
*A61N 1/00* (2006.01)
*A61N 1/368* (2006.01)
(Continued)

(52) U.S. Cl.
CPC .............. *A61N 1/368* (2013.01); *A61N 1/3628* (2013.01); *A61N 1/3987* (2013.01)

(58) Field of Classification Search
CPC .................................................. A61N 1/3605
USPC ............................................. 607/7, 9, 11, 74
See application file for complete search history.

(56) References Cited

U.S. PATENT DOCUMENTS 5,174,286 A    12/1992   Chirife
6,343,232 B1*   1/2002   Mower .............................. 607/9
(Continued)

FOREIGN PATENT DOCUMENTS

EP            1023917          8/2000

OTHER PUBLICATIONS

International Search Report and Written Opinion dated Dec. 6, 2012 for corresponding international patent application No. PCT/IB2012/053762.

(Continued)

*Primary Examiner* — Nicole F Lavert
*Assistant Examiner* — Nadia A Mahmood
(74) *Attorney, Agent, or Firm* — Abelman, Frayne & Schwab

(57) ABSTRACT

Pacemaker for the stimulation of the human heart having three electrodes or two electrodes, with the first electrode connected to the right atrium, the second electrode connected to the right ventricle and the third electrode connected to the said right ventricle. The pacemaker is programmed so that there is first stimulation of the right atrium by means of the first electrode, then there is second stimulation of the right ventricle by means of the second electrode with an interval function of the programmed AV delay (50-400 msec) and with a voltage not exceeding 80-90% of the threshold potential, and finally there is third stimulation, again of the right ventricle by means of the third electrode with a voltage that conforms with Safety Margin rules and at a second stimulation time interval comprised between 50 msec and 300 msec.

4 Claims, 3 Drawing Sheets

(51) Int. Cl.
*A61N 1/362* (2006.01)
*A61N 1/39* (2006.01)

(56) References Cited

U.S. PATENT DOCUMENTS 6,725,093 B1 4/2004 Ben-Haim
2008/0234772 A1* 9/2008 Shuros et al. .................. 607/11

OTHER PUBLICATIONS

International Preliminary Report on Patentability dated Oct. 22, 2013 for corresponding international patent application No. PCT/IB2012/053762.

Windle J R et al., Subthreshold conditioning stimuli prolong human ventricular refractoriness, American Journal of Cardiology, vol. 57, No. 6, Feb. 15, 1986, pp. 381-386.

* cited by examiner (STATE OF THE ART)

(STATE OF THE ART)

ATRIAL
ELECTRODE

VENTRICULAR
ELECTRODE

HEART STIMULATION DEVICE AND RESPECTIVE CONTROL SYSTEM

CROSS-REFERENCE TO RELATED APPLICATIONS

This application is a National Phase of PCT/IB2012/053762, filed 24 Jul. 2012, which claims priority from Italian Application No. RM2011A000429, filed 8 Aug. 2011, the disclosures of which are all incorporated herein by reference.

FIELD OF THE INVENTION

The present invention relates to a control process for a pacemaker or a defibrillator to be necessarily implanted in the body of patients with indication for implantation of a pacemaker or defibrillator and with particular heart conditions and electively in all other patients with indication for implantation of a pacemaker or defibrillator.

BACKGROUND OF THE INVENTION

The first pacemakers were provided with a single electrode, which was implanted on one or two ventricles of the heart of the sick patient, and epicardial stimulation was only performed on the ventricle to which said electrode was connected in those pathological cases in which the heart did not contract on its own or did not adequately contract. The implants were performed with a thoracotomy or subxiphoid approach. In 1967, pacemaker implantation became endocardial, i.e. the stimulating electrode was inserted transvenously into the right ventricle; the intervention is considerably less invasive.

In a subsequent development phase, greater clinical knowledge, improved implantation techniques, significant evolution of the pacemakers both from a stoichiometric and circuital point of view, and significant improvement of the stimulating electrodes, it was also proposed to place only one electrode in the atrium, as an alternative to connecting the electrode to the ventricle alone, a much more physiological solution in the case of particular clinical pictures.

In a subsequent phase pacemakers 1, which had two electrodes 3 and 4, were also developed and in this case an electrode 4 was positioned in the right ventricle and the other electrode 3 was positioned in the right atrium, cf. FIG. 1. The surgical operation for implantation of these pacemakers, known as dual-chamber or sequential pacemakers, was more complicated given the presence of two electrodes, thus they were only preferred in those heart conditions that justified the increased risk. Subsequently, with the progress of implantation techniques and the progress of the electrode technology, there was an increasing choice of dual-chamber pacemakers; since 1995, implanting a pacemaker means implanting a dual-chamber pacemaker unless there are clinical contraindications.

Given their clinical conditions, some patients require particular, more complex stimulations than the sequential, right atrium-ventricle stimulation. Such patients have serious conditions, i.e. they have an ejection fraction of less than 35% and are in NYHA class III or IV. So as to improve the clinical picture, i.e. to improve stroke volume and cardiac output, in addition to the atrial electrode 5 in the right atrium RA and the right ventricular electrode 6 in the right ventricle RV, in these patients there is also inserted a third electrode 7 in the left ventricle LV to also stimulate this part of the heart 20 with programmed times compared to the stimulation of the right ventricle, cf. FIG. 2. In such patients, depending on the clinical picture, there can be implanted a defibrillator 2 instead of a pacemaker; it should be borne in mind that a defibrillator also performs the functions of a pacemaker and that such functions are suitably controlled by the control programme of the pacemaker-defibrillator device.

For these patients, for whom it is necessary to implant a third electrode in the left ventricle in addition to the two electrodes in the right ventricle and atrium, there is nevertheless envisaged an implantation surgical operation that is often particularly lengthy and therefore very dangerous due to the very fact that it is performed on patients whose heart is particularly weakened, with risk to their life in the course of the operation. The difficulty of such an operation results from the need to make the third electrode cross the coronary sinus to reach the affixing position above the left ventricle inside the great cardiac vein. There are sometimes particular difficulties that advise against implanting the third electrode adapted to stimulate the left ventricle, and that are generally linked to the clinical conditions of the patient.

SUMMARY OF THE INVENTION

The primary aim of the present invention is that of creating a new, dual-chamber pacemaker or defibrillator with improved stimulation sequence (later also defined DBS=Dual Better Stimulation) more precisely described hereunder, which allows the achievement, with just two electrodes, of the same haemodynamic advantages as obtained with a triple-chamber implant pacemaker or defibrillator device of the prior art that requires three electrodes being arranged in the right atrium, right ventricle and left ventricle, as described in the "Background Of The Invention" section above and shown in FIG. 2.

Another important object is that of creating a pacemaker or defibrillator control process with three electrodes, but with two electrodes implanted in the right ventricle and one in the right atrium but utilising improved stimulation sequence, to improve, or at least maintain at the same level, the stroke volume and cardiac output compared to pacemakers or defibrillators controlled in accordance with the control processes of the prior art.

According to a first aspect of the invention, these aims are achieved by means of a stimulation device, in particular a pacemaker or defibrillator, comprising an atrial electrode adapted to be connected with the right atrium of the human heart, at least a first ventricular electrode adapted to be connected to the right ventricle of the human heart and provided with a control system, programmed to emit in the course of each cardiac stimulation cycle: a stimulation of the right atrium by means of the atrial electrode, a first stimulation of the right ventricle, defined below threshold pre-stimulus, by means of the at least one first ventricular electrode after a time interval T1, with a voltage comprised between 0.5 and −3 Volt and which does not exceed 80-90% of the cardiac stimulation threshold potential, a second stimulation of the right ventricle, after a time interval T2 of the predefined pre-stimulus comprised between 50 and 400 msec, with a voltage determined by the requirements of the human heart.

According to a further aspect of the invention, the above-mentioned aims are achieved by means of a stimulation device of the heart of a human being, in particular a pacemaker or defibrillator provided with a single atrial electrode and with a single ventricular electrode adapted to implementing a stimulation method of the type described.

Thanks to the invention, with a new dual-chamber pacemaker or defibrillator having only two electrodes, one connected in the right atrium and the other in the right ventricle, and programmed so as to produce a sequential stimulation between the stimulus in the atrium and the pre-stimulus in the right ventricle V1 with predefined delay time linked to the programmed AV delay and thereafter performing a second sequential stimulation V2 at V1, with both the stimuli in the right ventricle with a predefined and optimised delay between these two stimuli, known as VV delay, which resulted as being optimal between 70 and 80 msec, there is obtained the maximum stroke volume and cardiac output that can be delivered by the heart of the particular patient in whom the device is implanted, thus guaranteeing the important advantage of reducing the invasiveness of the implant operation of the device. It should be noted that the stimulus V1, i.e. the first in the ventricle, must necessarily have the above-described characteristics.

In the alternative variant of the method of the invention, wherein three-electrode stimulation devices are used, which are however implanted by means of a much simpler and quicker surgical operation, i.e. by positioning the first electrode in the right atrium, the second in the right ventricle and the third again in the right ventricle, and programmed to provide sequential AV stimulation and with a dual sequential V1 and V2 stimulation in the right ventricle, of the DBS type, through the two electrodes with delay between the two programmable stimuli, known as VV delay, the same, above-listed advantages for the patient are achieved.

Indeed, in each of the alternatives, implementation of the first ventricular stimulation, whether performed through a single electrode or through two electrodes in the right ventricle, by emitting a first impulse having a voltage which does not exceed 80-90% of the threshold potential, defined "below threshold stimulation", of a duration comprised between 0.1-1.0 msec, and which has been found to be optimal at 0.4 msec, followed by a second ventricular impulse capable of provoking a cardiac contraction having an amplitude that conforms with the Safety Margin rule, widely used in this type of operation, and after an interval of time from the first ventricular stimulation comprised between 50 msec and 300 msec, produces the desired results.

In the case in which the control process object of the present invention is utilised in a pacemaker or defibrillator with three electrodes, there is nevertheless the great advantage that these electrodes are inserted into just two chambers instead of into three chambers, an operation that entails a significant simplification of the surgical intervention for implanting the device in that it is much less invasive and much quicker.

The dependent claims describe preferred embodiments of the invention.

BRIEF DESCRIPTION OF THE DRAWINGS

Further characteristics and advantages of the invention will become clearer in the light of the detailed description of a preferred but non-exclusive embodiment of a stimulation device for the stimulation produced by a pacemaker or defibrillator, illustrated by way of a non-limiting example, with the assistance of the accompanying drawings, wherein.

The same reference numbers in the drawings identify the same elements or components.

DETAILED DESCRIPTION OF PREFERRED EMBODIMENTS OF THE INVENTION

Figure 1:
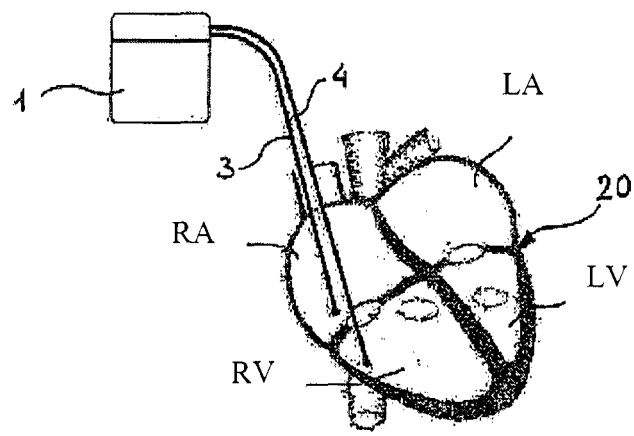
FIG. 1 shows a schematic, cross-sectional view of a heart with sequential, dual-chamber stimulation device with two electrodes implanted as in the prior art.
Figure 2:
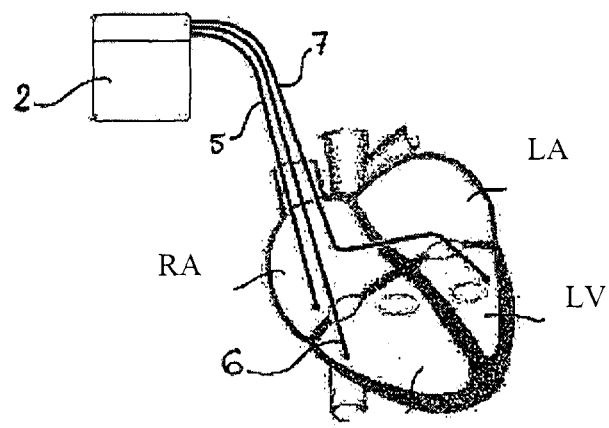
FIG. 2 shows a schematic, cross-sectional view of a heart with sequential, three-chamber stimulation device with three electrodes implanted as in the prior art.
Figure 3:
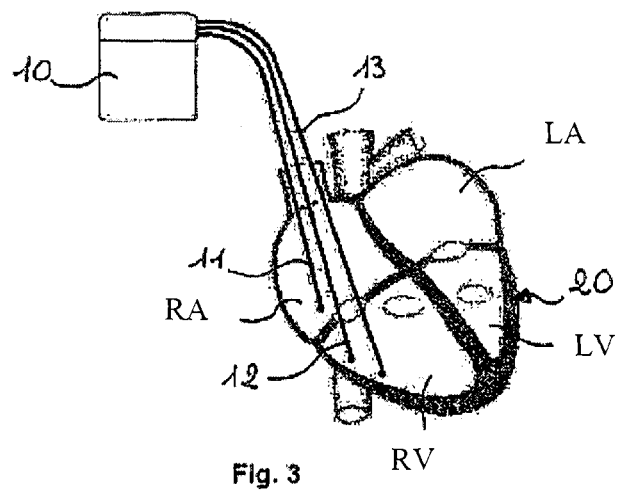
FIG. 3 shows a schematic, cross-sectional view of a heart associated with a stimulation device having three electrodes implanted and programmed according to the invention.

With particular reference to FIG. 3, the first solution proposed by the present invention is that of stimulating the heart 20 with DBS stimulation with a pacemaker or defibrillator 10 having three electrodes with two electrodes 12 and 13 in the right ventricle with sequential stimulation and one electrode 11 in the right atrium. This solution is particularly suitable in those cases in which the stimulation device 10 already on the market has three electrodes and has the possibility of being programmed so as to emit a sequence of successive stimulations through each electrode during each cardiac stimulation cycle. Or by the second solution proposed by the present invention with pacemaker or defibrillator 15 having two electrodes with one electrode 16 in the right atrium RA and one electrode 17 in the right ventricle RV, which allows a DBS stimulation. This solution can be achieved with a device having just two electrodes, but that must be provided with means that, when suitably programmed, allow the single ventricular electrode 17 to emit two stimuli in the course of the same cardiac stimulation cycle, having the duration $T_0$. Both the solutions described herein allow substitution of the three-chamber stimulation while achieving the same haemodynamic advantages.

The electrodes, whether there are two or three, are positioned inside the right atrium RA and the right ventricle RV on the basis of the intraoperative measures, such as in the implant, normally without other precautions, while exclusively following the usual rules known to all expert implanters of this type of implant.

The natural contraction between the left ventricle LV and the right ventricle RV in human hearts occurs at a time interval comprised between 5 and 20 msec; should this time interval exceed 50 msec, the heart pumps incorrectly.

The succession of the two stimuli in the right ventricle RV must be made in a very particular way to permit correct contraction of the left ventricle LV so that there is good stroke volume and cardiac output; this determines the programming of the pacemaker when it is implanted in the patient's body.

Thus in accordance with the invention, in its first aspect, when we consider the solution wherein the stimulation device has three electrodes as in FIG. 3, after the normal atrial stimulation that marks the start of cardiac stimulation cycle, which has an overall duration $T_0$, following the time interval $T_1$, the right ventricle RV is first stimulated with the electrode 12. This stimulus, defined a pre-stimulus for the purposes of this description, is produced with an impulse having a "BELOW THRESHOLD" voltage, e.g. if for a certain patient, stimulation of the heart 20 requires the amplitude of 1 Volt for an impulse duration equal to 0.50 msec, this pre-stimulus must be of a duration equal to 0.40 msec and of an amplitude equal to 80 to 90% of the threshold stimulus. The pre-stimulus does not cause the same contractive effects on the cardiac muscles as a normal atrial or ventricular stimulus. After a time interval $T_2$ comprised between 50 and 400 msec from the pre-stimulus, the right ventricle RV is stimulated by means of the second ventricular electrode 13 with an impulse adapted to provoke a cardiac contraction of an amplitude and duration that is in line with the Safety Margin rules. The time interval T1+T2 is habitually defined as atrioventricular delay AV, while T2 is habitually defined ventricular sequence delay.

The time interval $T_2$ between the pre-stimulus performed by the first ventricular electrode 12 in the right ventricle RV and the simulation performed by the second ventricular electrode 13 in the right ventricle RV is identified by detection methods of the known type by means of the programmer of the implanted pacemaker or defibrillator; in fact the first electrode 12 of the right ventricle is inserted in the inlet of the connector of the pacemaker or defibrillator designated for the electrode of the left ventricle LV, while the second electrode 13 of the right ventricle RV is inserted into the inlet of the connector designed for the electrode of the right ventricle RV. The inventor has discovered that the pre-stimulus causes a pre-excitation that contributes to more quickly transmitting the stimulus emitted by the second electrode to the left ventricle thus significantly improving stroke volume and cardiac output.

Stimulation takes place in the normal sequence of the pacemakers or defibrillators, i.e. first the right atrium RA is stimulated; following an interval T1 function of the delay AV programmed (AV=T1+T2=50-400 msec), the right ventricle RV is stimulated with a pre-stimulus having BELOW THRESHOLD voltage by means of the first electrode 12 of the electrodes of the right ventricle RV and subsequently, after a time $T_2$, there is activated the stimulation of the second electrode 13 of the right ventricle RV with stimulus adapted to causing a cardiac contraction having a volt amplitude that is in line with Safety Margin rules.

Thus, the implant of two electrodes 12 and 13 in the right ventricle RV without any electrode being implanted in the left ventricle LV and with a third electrode 11 connected to the right atrium RA, controlled with the just-described sequence of stimuli, guarantees a correct succession of the contractions of all the cavities of the heart that contribute to optimal pumping of the blood.

The implant of three electrodes wherein two electrodes are in the right ventricle RV, therefore guarantees the same cardiac output and stroke volume as an implant that is provided with three electrodes, each in separate chambers.

The particularly positive results of the stimulus according to the method of the invention on cardiac output, are shown in the following table, which presents comparative results on a group of five patients, compared to the results obtained utilising a classic, biventricular heart stimulation methodology.

The table does not present atrial stimulation data, which remain unchanged irrespective of whether the stimulation takes with a method that conforms to the prior art or with the method of the invention.

TABLE

Comparison between bi-cameral (A + V) stimulation and bi-cameral tri-focal (A + $V_1$ + $V_2$) stimulation using DBS procedure*
Measurement of stroke volume (SV) and cardiac output (CO)

| patient # | Id. age sex base ECG date | compared measurement (stimulating electrode) | PM program. | $V_2$ setting | $V_1$ setting amplitude (volt) | $D_t$ (msec) | $V_1V_2$ interval (msec) | stimulation type | SV (ml) | CO (lpm) | CO increase with DBS (lpm) |
|---|---|---|---|---|---|---|---|---|---|---|---|
| 1 | PE 77 ♀ AF May 17, 2012 | only $V_2$ both $V_1$ and $V_2$ | VVI VVI + DBS | standard standard | 0.60 0.60 | 0.40 0.40 | 70 70 | $V_2$: tip-ring $V_1$: tip-ring; $V_2$: tip-ring | 23,000 29,000 | 2,051 2,611 | 0.560 |
| 2 | MG 81 ♂ total AVB Jan. 19, 2012 | only $V_2$ both $V_1$ and $V_2$ | DDD DDD + DBS | standard standard | 2.60 2.60 | 0.40 0.40 | 70 70 | $V_2$: tip-ring $V_1$: tip-canister; $V_2$: tip-ring | 42,992 49,980 | 2,580 3,020 | 0.440 |
|  | optimization of PM parameters May 24, 2012 | only $V_2$ both $V_1$ and $V_2$ | DDD DDD + DBS | standard standard | 2.60 2.60 | 0.40 0.40 | 70 70 | $V_2$: tip-ring $V_1$: tip-canister; $V_2$: tip-ring | 60,000 71,000 | 3,741 4,421 | 0.680 |
| 3 | VA 66 ♂ total AVB Dec. 14, 2011 | only $V_2$ both $V_1$ and $V_2$ | DDD DDD + DBS | standard standard | 2.40 2.40 | 0.40 0.40 | 70 70 | $V_2$: tip-ring $V_1$: tip-canister; $V_2$: tip-ring | 93,990 99,000 | 6,180 6,450 | 0.270 |
|  | optimization of PM parameters Nov. 04, 2012 | only $V_2$ both $V_1$ and $V_2$ | DDD DDD + DBS | standard standard | 2.40 2.40 | 0.10 0.10 | 70 70 | $V_2$: tip-ring $V_1$: tip-canister; $V_2$: tip-ring | 86,975 94,983 | 5,838 6,160 | 0.322 |
| 4 | BA 80 ♀ AF Sep. 14, 2011 | only $V_2$ both $V_1$ and $V_2$ | VVI VVI + DBS | standard standard | 0.70 0.70 | 0.50 0.50 | 80 80 | $V_2$: tip-ring $V_1$: tip-ring; $V_2$: tip-ring | 56,000 63,000 | 3,934 4,410 | 0.476 |
|  | optimization of PM parameters Dec. 21, 2011 | only $V_2$ both $V_1$ and $V_2$ | VVI VVI + DBS | standard standard | 0.70 0.70 | 0.40 0.40 | 70 70 | $V_2$: tip-ring $V_1$: tip-ring; $V_2$: tip-ring | 51,984 58,996 | 3,660 4,140 | 0.480 |
| 5 | SSA 89 ♂ total AVB Sep. 20, 2011 | only $V_2$ both $V_1$ and $V_2$ | DDD DDD + DBS | standard standard | 1.50 1.50 | 1.50 1.50 | 70 70 | $V_2$: tip-ring $V_1$: tip-canister; $V_2$: tip-ring | 82,998 91,977 | 5,820 6,413 | 0.593 |
|  | optimization of PM parameters Dec. 14, 2011 | only $V_2$ both $V_1$ and $V_2$ | DDD DDD + DBS | standard standard | 1.00 1.00 | 0.40 0.40 | 70 70 | $V_2$: tip-ring $V_1$: tip-ring; $V_2$: tip-ring | 81,928 93,942 | 5,684 6,630 | 0.946 |

*Electrode $V_1$ stimulates below threshold; electrode $V_2$ stimulates in standard mode It is important to note that column C1 indicates for each patient the stimulation methods with a single ventricular electrode V2 emitting a single stimulus adapted to provoke a cardiac contraction and the DBS method with two electrodes and two stimuli V1 and V2 in the right ventricle RV. The column C2 records the data relating to the increase in cardiac output when stimulation is applied on the same patient with the single electrode V2 as is envisaged in the stimulation devices of the prior art and when stimulation is applied with the two stimuli V1 and V2 through two electrodes of the right ventricle RV with DBS stimulation, in line with the present invention.

Figure 4:
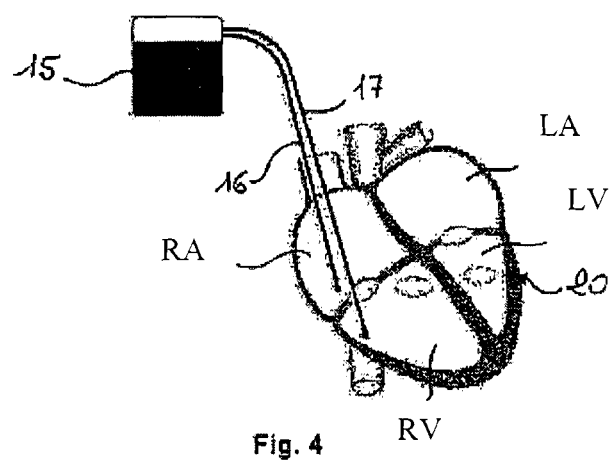
FIG. 4 shows a schematic, cross-sectional view of a heart associated with a new, dual-chamber sequential stimulation device with two electrodes implanted and programmed according to the invention.
Figure 5:
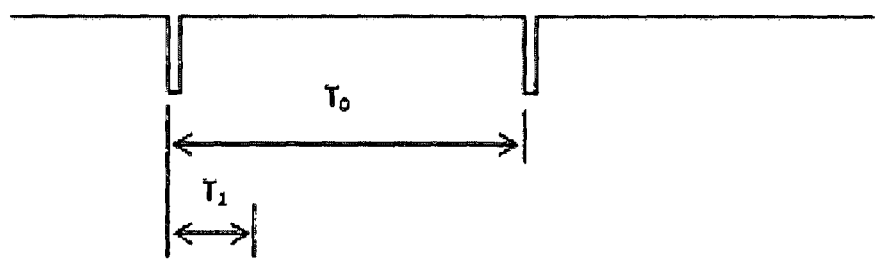
FIG. 5 represents a diagram of the stimulation of the human heart by means of a pacemaker or defibrillator programmed according to the invention.
Figure 5:
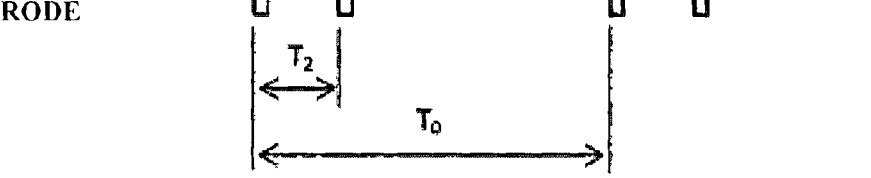

With particular reference to FIG. 4, in the second solution according to the invention with pacemaker or defibrillator 15 having only two electrodes, a first electrode 16, known as the atrial electrode, is implanted in the right atrium RA and the second ventricular electrode 17 is implanted in the right ventricle RV. With this solution there is obtained the same result by programming the stimulation device with the stimulation method of the invention DBS, i.e. three impulses, wherein the first impulse is emitted in the right atrium RA with the atrial electrode 16 followed, after the interval $T_1$, by a pre-impulse having BELOW THRESHOLD voltage in the right ventricle RV through the ventricular electrode 17 implanted in the right ventricle RV. This ventricular pre-impulse is followed by a second ventricular impulse emitted sequentially following a delay T2, again through the single ventricular electrode 17 with predefined intensity, as already described for the preceding solution of FIG. 3. The sequence of impulses emitted during a cardiac stimulation cycle $T_0$ is the sequence illustrated in the diagram of FIG. 5 and already explained above in the description.

This second solution envisaged that the stimulation device 15, of the new type, comprises an electronic circuit capable of emitting three impulses: one in the right atrium and two subsequent impulses in the right ventricle, through the said ventricular electrode 17 during the said cardiac stimulation cycle $T_0$.

Thanks to this configuration, the same haemodynamic advantages as described above are obtained, but with less invasiveness than the previous variant with stimulation device having three electrodes.

The simplicity of each of the above-described variants of pacemaker or defibrillator is such that this type of intervention must be applied not only in patients with special conditions but in all patients with indication for pacemaker or defibrillator.

The invention claimed is:

1. A dual-chamber pacemaker comprising:
an atrial electrode adapted to be connected to the right atrium of the human heart of a patient,
at least one first ventricular electrode adapted to be connected to the right ventricle of the human heart, and
a control system that has been arranged to emit, in the course of each cardiac stimulation cycle:
a first impulse for the stimulation of the right atrium by means of the atrial electrode,
a second impulse for a first stimulation of the right ventricle, said first stimulation being defined below-threshold pre-stimulation, by means of the at least one first ventricular electrode, said second impulse being emitted after a time interval T1 from the emission of the first impulse, this second impulse having a voltage comprised between 0.5 and −3 Volt and which is not in excess of 80-90% of the cardiac stimulation threshold potential of the patient,
a third impulse for a second stimulation of the right ventricle, emitted after a time interval T2 from the predefined pre-stimulation second impulse, said time interval T2 being comprised between 50 and 400 msec, said third impulse having a voltage adapted to provoke the cardiac stimulation of the patient;
wherein the dual-chamber pacemaker does not include any electrode in the left ventricle of the human heart.

2. A dual-chamber pacemaker according to claim 1, wherein said third impulse for the second stimulation of the right ventricle is emitted by means of the at least one first ventricular electrode.

3. A dual-chamber pacemaker according to claim 1, provided with a second ventricular electrode adapted to be connected to the right ventricle and wherein said second stimulation of the right ventricle occurs by means of the second ventricular electrode.

4. A dual-chamber pacemaker according to claim 1, wherein said time interval T2 from the first stimulation of the right ventricle is equal to 70 msec.

* * * * *